United States Patent
Yano et al.

(10) Patent No.: US 8,960,122 B2
(45) Date of Patent: Feb. 24, 2015

(54) APPARATUS AND METHOD FOR MANUFACTURING ABSORBENT BODY

(75) Inventors: Takanori Yano, Kagawa (JP); Makoto Suzuki, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 932 days.

(21) Appl. No.: 13/054,173

(22) PCT Filed: Jul. 29, 2009

(86) PCT No.: PCT/JP2009/063472
§ 371 (c)(1),
(2), (4) Date: Mar. 4, 2011

(87) PCT Pub. No.: WO2010/013736
PCT Pub. Date: Feb. 4, 2010

(65) Prior Publication Data
US 2011/0165322 A1   Jul. 7, 2011

(30) Foreign Application Priority Data

Jul. 31, 2008  (JP) ................................. 2008-198347

(51) Int. Cl.
*B05C 19/04* (2006.01)
*B29C 41/50* (2006.01)
(Continued)

(52) U.S. Cl.
CPC ..... *A61F 13/15658* (2013.01); *A61F 13/15626* (2013.01); *D04H 1/72* (2013.01); *A61F 2013/530489* (2013.01)
USPC ........... 118/308; 425/80.1; 425/83.1; 425/90; 156/276; 156/285

(58) Field of Classification Search
CPC .................... A61F 13/15626; A61F 13/15658
USPC ........... 118/308; 425/80.1, 81.1, 83.1, 90, 91; 264/112, 113, 119, 279, 294, 297.1, 264/297.6, 299, 308, 309, 511, 517, 546, 264/553, 571; 156/276, 285, 383, 436
See application file for complete search history.

(56) References Cited

U.S. PATENT DOCUMENTS 4,388,056 A * 6/1983 Lee et al. ..................... 425/83.1
(Continued)

FOREIGN PATENT DOCUMENTS

CN           1470226 A       1/2004
(Continued)

OTHER PUBLICATIONS

English Translation of CN1470226A, Jan. 28, 2004.*
(Continued)

*Primary Examiner* — Yewebdar Tadesse
(74) *Attorney, Agent, or Firm* — Brinks Gilson & Lione

(57) ABSTRACT

An apparatus for manufacturing an absorbent body, including a recessed form die formed on a predetermined face of a predetermined member, moving in one direction along a moving path along the predetermined face; a duct disposed in a predetermined position in the moving path, discharging a gas including fluid absorbent fibers from an opening section toward the predetermined face; and a polymer casting member disposed inside the duct, casting a superabsorbent polymer from a casting opening toward a center area of the opening section in a direction along the moving path, wherein in the case of the form die passing the duct position, by the gas being sucked through air intake holes in a bottom section of the form die, the fluid absorbent fibers and the superabsorbent polymer in the gas are stacked in the form die to form an absorbent body, wherein an air pressure inside the duct is made lower than the air pressure outside the duct because of the gas being sucked through the bottom section of the form die, wherein a duct-inner-wall section is inside the duct and is disposed facing an inner wall face of a wall section of the duct with a spacing therebetween, the wall section having a gap between the predetermined face and the opening section of the duct, and an outside air intrudes into the duct along the moving path through the gap, and the duct-inner-wall section restricts the outside air intruding into the duct through the gap flowing into the center area of the duct.

8 Claims, 7 Drawing Sheets

(51) Int. Cl.
*A61F 13/15* (2006.01)
*D04H 1/72* (2012.01)
*A61F 13/53* (2006.01)

(56) References Cited

U.S. PATENT DOCUMENTS

| | | | |
|---|---|---|---|
| 6,048,489 A * | 4/2000 | Reiter et al. | 264/510 |
| 6,848,894 B2 * | 2/2005 | Baker et al. | 425/81.1 |
| 6,877,970 B2 | 4/2005 | Tange et al. | |
| 8,187,524 B2 * | 5/2012 | Yano | 264/517 |
| 8,597,458 B2 * | 12/2013 | Taniguchi et al. | 156/276 |
| 2001/0054783 A1 | 12/2001 | Kobayashi et al. | |
| 2007/0244453 A1 | 10/2007 | Yasumura et al. | |
| 2011/0049758 A1 | 3/2011 | Takahashi et al. | |

FOREIGN PATENT DOCUMENTS

| | | |
|---|---|---|
| CN | 1261633 C | 6/2006 |
| EP | 2 255 765 A1 | 12/2010 |
| EP | 2 491 907 A1 | 8/2012 |
| EP | 2 491 908 A1 | 8/2012 |
| JP | 54-101982 | 8/1979 |
| JP | 10-137286 | 5/1998 |
| JP | 2001-288670 | 10/2001 |
| JP | 2002-317373 | 10/2002 |
| JP | 2003-278067 | 10/2003 |
| JP | 2004-065930 | 3/2004 |
| JP | 2006-16727 | 1/2006 |
| JP | 2006-122138 | 5/2006 |
| JP | 2006-132009 | 5/2006 |
| JP | 2008-132055 | 6/2008 |
| JP | 2008-154774 | 7/2008 |
| WO | WO 02/12605 A2 | 2/2002 |
| WO | WO 03/020193 A1 | 3/2003 |
| WO | WO 03/078719 A1 | 9/2003 |

OTHER PUBLICATIONS

International Search Report from corresponding PCT application No. PCT/JP2009/063472 dated Oct. 27, 2009, 4 pgs.

Chinese Office Action from corresponding Chinese application No. 200980129464.X dated Dec. 19, 2012, 11 pgs.

Chinese Second Office Action and English translation from corresponding Chinese Application No. 200980129464.X dated Aug. 21, 2013 (13 pgs).

European extended Search Report from corresponding European Application No. 09802978.8 dated Aug. 28, 2013 (7 pgs).

Japanese Notice from corresponding Japanese application No. 2008-198347 dated May 25, 2013, 6 pgs.

Japanese Office Action from corresponding Japan application No. 2008-198347 dated Mar. 7, 2013 and Google English translation, 4 pgs.

* cited by examiner

APPARATUS AND METHOD FOR MANUFACTURING ABSORBENT BODY

Related Application

The present application is a 35 U.S.C. §371 national stage filing of International Patent Application No. PCT/JP2009/063472, filed Jul. 29, 2009, to which priority is claimed under 35 U.S.C. §120 and through which priority is claimed under 35 U.S.C. §119 to Japanese Priority Patent Application No. 2008-198347, filed Jul. 31, 2008.

TECHNICAL FIELD

The present invention relates to an apparatus and a method for manufacturing an absorbent body of an absorbent article such as a disposable diaper.

BACKGROUND ART

As examples of an absorbent article that absorbs fluid, disposable diapers, sanitary napkins, and the like are used. These absorbent articles include an absorbent body 1 that is produced by forming pulp fibers into a predetermined shape. The absorbent body 1 is formed by a fiber stacking apparatus 10a in a production line. FIG. 1 is a side view of the fiber stacking apparatus 10a partially shown in a vertical cross-section. The fiber stacking apparatus 10a includes as the main body a rotating drum 20 that rotates in a circumferential direction Dc, and recessed form dies 21 are formed on an outer circumferential surface 20a of the rotating drum 20. And a bottom section of the form dies 21 are configured so that air intake is possible. Moreover, a distribution opening 31a of a duct 31 is provided so as to face the outer circumferential surface 20a of the rotating drum 20, and from the distribution opening 31a an air mixture 3 with the pulp fibers 2 mixed in is discharged toward the outer circumferential surface 20a.

Thus, in the case of the form die 21 passing the position of the distribution opening 31a as the rotating drum 20 rotates, the air mixture 3 discharged from the distribution opening 31a is sucked through the bottom section of the form die 21. And by suction forces generated inside the form die 21 in this way, the pulp fibers 2 in the air mixture 3 are stacked inside the form die 21 and thus formed into the absorbent body 1 (see PTL 1).

CITATION LIST

Patent Literature

PTL 1: JP-A-2006-132009

SUMMARY OF INVENTION

Technical Problem

By the way, a polymer casting member 38 for casting a superabsorbent polymer 5 (polymeric polymer having high holding performance for liquid such as water) into the absorbent body 1 is also disposed inside the duct 31. For the purpose of distributing the superabsorbent polymer 5 in the center portion of the absorbent body 1 in a width direction, the superabsorbent polymer 5 is discharged toward a center area Ac of the distribution opening 31a in the circumferential direction Dc. However in such case, it is preferable that the superabsorbent polymer 5 is accumulated in the absorbent body 1 while being dispersed and distributed uniformly by riding on the air mixture 3.

However, because of an outside air intruding into the duct 31, the air mixture 3 partially becomes turbulent and as a result, dispersion under uniform distribution of the superabsorbent polymer 5 (hereafter, refer to as uniform dispersion) may be impaired.

In detail, by the above mentioned air intake through the bottom section of the form dies 21 of the rotating drum 20, an air pressure inside the duct 31 is maintained lower than the air pressure outside the duct 31 (hereafter, referred to as a "negative pressure"). Thus, the outside air enters into the duct 31 especially through a gap G in an upstream side in the circumferential direction Dc and a gap G in a downstream side that are hard to include an attachment-style seal member, of the gaps G between the outer circumferential surface 20a of the rotating drum 20 and the distribution opening 31a of the duct 31. And this intruding outside air causes turbulence such as a vortex inside the duct 31, and as a result, may inhibit the uniform dispersion of the superabsorbent polymer 5 being casted toward the center area Ac.

The present invention was made in view of the foregoing conventional problem, and it is an advantage thereof to provide an apparatus and a method for manufacturing an absorbent body that can reduce effects of the outside air intruding into the duct on the uniform dispersion of the superabsorbent polymer.

Solution to Problem

A main aspect of the invention for achieving the foregoing object is an apparatus for manufacturing an absorbent body, including:
  a recessed form die formed on a predetermined face of a predetermined member, moving in one direction along a moving path along the predetermined face;
  a duct disposed in a predetermined position in the moving path, discharging a gas including fluid absorbent fibers from an opening section toward the predetermined face; and
  a polymer casting member disposed inside the duct, casting a superabsorbent polymer from a casting opening toward a center area of the opening section in a direction along the moving path,
  wherein in the case of the form die passing the duct position, by the gas being sucked through air intake holes in a bottom section of the form die, the fluid absorbent fibers and the superabsorbent polymer in the gas are stacked in the form die to form an absorbent body,
  wherein an air pressure inside the duct is made lower than the air pressure outside the duct because of the gas being sucked through the bottom section of the form die,
  wherein a duct-inner-wall section is inside the duct and is disposed facing an inner wall face of a wall section of the duct with a spacing therebetween, the wall section having a gap between the predetermined face and the opening section of the duct, and
  an outside air intrudes into the duct along the moving path through the gap, and the duct-inner-wall section restricts the outside air intruding into the duct through the gap flowing into the center area of the duct.

And also a main aspect of the invention for achieving the foregoing object is a method for manufacturing an absorbent body, including:
forming an absorbent body by stacking fluid absorbent fibers and a superabsorbent polymer in a gas in a form die, in the case of the form die passing a duct position, by sucking the gas through air intake holes in a bottom section of the form die using a recessed form die formed on a predetermined face of a predetermined member, moving in one direction along a moving path along the predetermined face;

a duct disposed in a predetermined position in the moving path, discharging the gas including the fluid absorbent fibers from an opening section toward the predetermined face; and a polymer casting member disposed inside the duct, casting the superabsorbent polymer from a casting opening toward a center area of the opening section in a direction along the moving path, wherein an air pressure inside the duct is made lower than the air pressure outside the duct because of the gas being sucked through the bottom section of the form die, wherein a duct-inner-wall section is inside the duct and is disposed facing an inner wall face of a wall section of the duct with a spacing therebetween, the wall section having a gap between the predetermined face and the opening section of the duct, and an outside air intrudes into the duct along the moving path through the gap, and the duct-inner-wall section restricts the outside air intruding into the duct through the gap flowing into the center area of the duct.

Other features of the invention will become clear by the description of the present specification and the accompanying drawings.

Advantageous Effects of Invention

According to the present invention, effects of the outside air intruding into the duct on the uniform dispersion of the superabsorbent polymer can be reduced.

DESCRIPTION OF EMBODIMENTS

Figure 1:
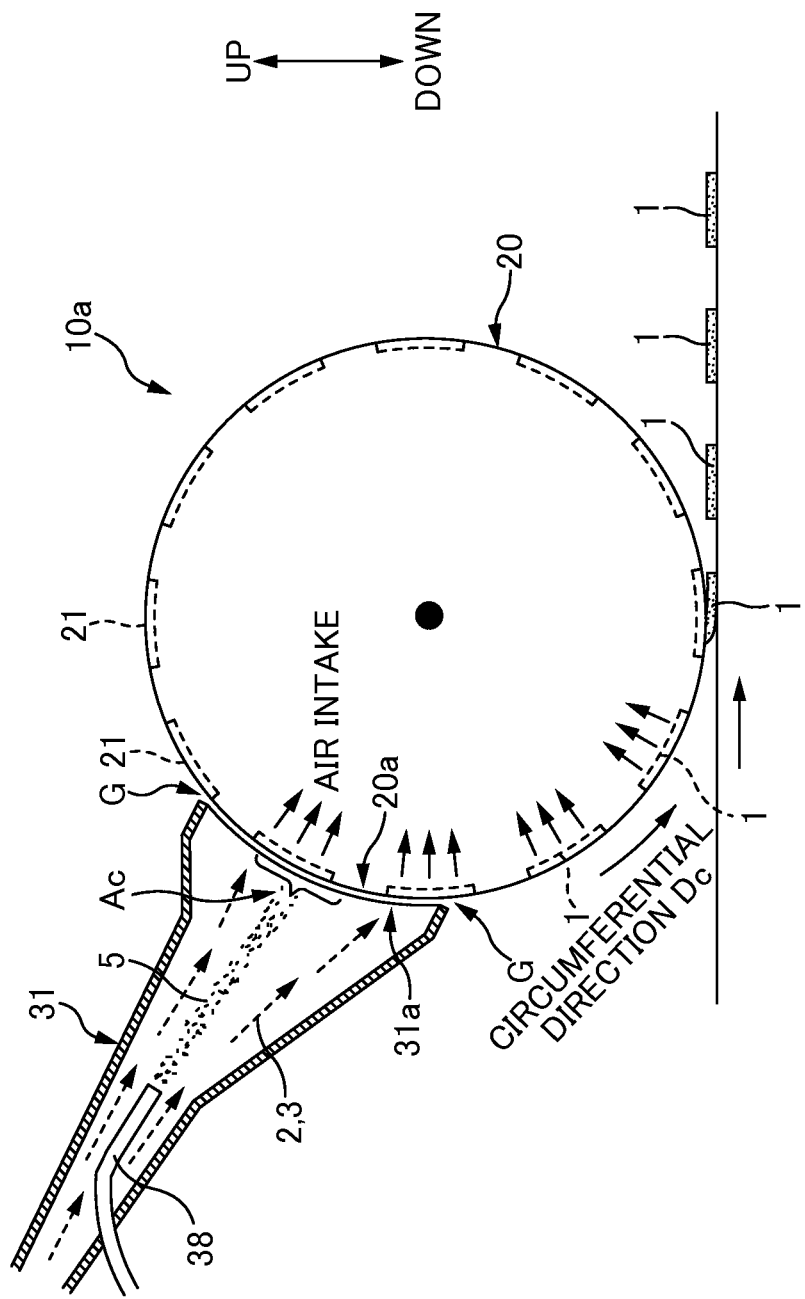
FIG. 1 is a side view of a fiber stacking apparatus 10a partially shown in a vertical cross-section.

At least the following matters will be made clear by the description in the present specification and the accompanying drawings.

An apparatus for manufacturing an absorbent body, including:

a recessed form die formed on a predetermined face of a predetermined member, moving in one direction along a moving path along the predetermined face;

a duct disposed in a predetermined position in the moving path, discharging a gas including fluid absorbent fibers from an opening section toward the predetermined face; and a polymer casting member disposed inside the duct, casting a superabsorbent polymer from a casting opening toward a center area of the opening section in a direction along the moving path, wherein in the case of the form die passing the duct position, by the gas being sucked through air intake holes in a bottom section of the form die, the fluid absorbent fibers and the superabsorbent polymer in the gas are stacked in the form die to form an absorbent body, wherein an air pressure inside the duct is made lower than the air pressure outside the duct because of the gas being sucked through the bottom section of the form die, wherein a duct-inner-wall section is inside the duct and is disposed facing an inner wall face of a wall section of the duct with a spacing therebetween, the wall section having a gap between the predetermined face and the opening section of the duct, and an outside air intrudes into the duct along the moving path through the gap, and the duct-inner-wall section restricts the outside air intruding into the duct through the gap flowing into the center area of the duct.

According to this apparatus for manufacturing an absorbent body, in which a duct-inner-wall section is included, the duct-inner-wall section can prevent the outside air intruding into the duct through the gap flowing into the center area of the duct. Thus, effects of turbulence or the like caused by the intruding outside air can be suppressed efficiently in the center area where the superabsorbent polymer is being casted, and as a result the uniform dispersion of the superabsorbent polymer can be performed.

In the apparatus for manufacturing an absorbent body, it is preferable that a flowing path of the gas flowing through the duct toward the predetermined face is divided, by the duct-inner-wall section, into an end-side flowing path that flows through the spacing between the inner wall face and the duct-inner-wall section, and a center-side flowing path that flows through the center area, and in the end-side flowing path, the spacing of an end section in an upstream side is made narrower than the spacing of an end section in a downstream side.

According to this apparatus for manufacturing an absorbent body, in the case of the gas passing the end section in the upstream side, since the spacing is narrow a flowing speed of the gas increases and the flow becomes stable. And the increased flowing speed is largely maintained because of the adjacent form die on the predetermined face sucking the gas even the spacing becomes wider in the end section in the downstream side. That is, the flow is kept in the stable state. As a result, generation of turbulence can be suppressed in a space in the vicinity of the predetermined face which is adjacent to the end section of the end-side flowing path in the downstream side, and the stack distribution of the fluid absorbent fibers can be made uniform.

In the apparatus for manufacturing an absorbent body, it is preferable that a flowing path of the gas flowing through the duct toward the predetermined face is divided, by the duct-inner-wall section, into an end-side flowing path that flows through the spacing between the inner wall face and the duct-inner-wall section, and a center-side flowing path that flows through the center area, and in a portion in a downstream side in the end-side flowing path the spacing becomes wider toward the downstream side, and in a portion in an upstream side in the end-side flowing path a portion having an uniform spacing over a predetermined length along the flowing path is included.

According to this apparatus for manufacturing an absorbent body, the flow of the gas is fixed and stabilized while flowing through the portion having the uniform spacing, because the portion in the upstream side in the end-side flowing path includes the portion having the uniform spacing over a predetermined length along the flowing path, and thus the flow of the gas is in a state of approximate laminar flow. And the gas in the state of approximate laminar flow reaches the form die on the predetermined face and thereby the stack distribution of the fluid absorbent fibers can be made uniform.

In the apparatus for manufacturing an absorbent body, it is preferable that the duct-inner-wall section is respectively provided to the wall section positioned in an upstream side in the direction along the moving path and the wall section positioned in a downstream side, of the wall sections of the duct, and a flowing path of the gas flowing through the duct toward the predetermined face is divided into three, by the duct-inner-wall sections, in respect to the direction along the moving path.

According to this apparatus for manufacturing an absorbent body, it is possible to prevent both of the outside air intruding into the duct through the gap in the upstream side in the direction along the moving path and the outside air intruding into the duct through the gap in the downstream side, of the gaps, flowing into the center area of the duct. Thus, generations of turbulence caused by the intruding outside air can be suppressed efficiently in the center area where the superabsorbent polymer is being casted, and as a result the uniform dispersion of the superabsorbent polymer can be performed.

Further, the flowing path of the gas is divided into three in respect to the direction along the moving path and the superabsorbent polymer is casted through a middle flowing path. Thus the absorbent body with a three-layer structure, that is, the absorbent body including an intermediate layer with a high mixture ratio of the superabsorbent polymer in the middle of the absorbent body in the thickness direction, and an upper layer and a lower layer sandwiching the intermediate layer with high mixture ratios of the fluid absorbent fibers can be surely formed.

In the apparatus for manufacturing an absorbent body, it is preferable that the wall section of the duct is formed in a shape in which a predetermined region of the wall section is swelling out in the direction along the moving path than a surrounding region, a predetermined swelling out region is positioned in the predetermined face side starting at a predetermined swelling-out start position, the duct-inner-wall section is provided in the position in the predetermined face side than the swelling-out start position, and a space in the predetermined swelling out region is filled by the duct-inner-wall section, and at a same time a flowing path of the gas flowing through the duct toward the predetermined face is divided, by the duct-inner-wall section, into an end-side flowing path that flows through a spacing between the inner wall face and the duct-inner-wall section, and a center-side flowing path that flows through the center area.

According to this apparatus for manufacturing an absorbent body, the turbulence that may occur in the swelling out region because of rapid enlargement of a cross-sectional area of the flowing path can be suppressed efficiently by the duct-inner-wall section. As a result, the stack distribution of the fluid absorbent fibers can be made uniform.

In the apparatus for manufacturing an absorbent body, it is preferable that a plurality of the form dies are intermittently formed in the direction along the moving path, a portion in which the form die is not formed between the form dies on the predetermined face is impervious to air, and size of a spacing between an end portion of the duct-inner-wall section in the predetermined face side and an end portion of the inner wall face of the duct in the predetermined face side is longer than a length of the above mentioned non-form-die-formed portion in the direction along the moving path.

According to this apparatus for manufacturing an absorbent body, pulsing of air pressure in the space of the spacing can be lessened while the form die moves along the moving path. As a result, the generation of the turbulence in the space is prevented, and stack distribution of the fluid absorbent fibers can be made uniform.

Detail is as follows. First, in the above configuration, the air intake is performed through the form die, however the air intake is not performed through the non-form-die-formed portion between the form dies. Thus, an atmospheric pressure in the spacing decreases in the case of the form die passing, and increases in the case of the non-form-die-formed portion passing. And, this periodical change in atmospheric pressure becomes greater especially in a case where the non-form-die-formed portion covers the space of the spacing, thus causing a state in which none of the air is sucked from the space.

In such respect, in the above configuration, by making the length of the spacing longer than the length of the non-form-die-formed portion, the space is consistently covered by at least a part of the form die. That is, in the case where the non-form-die-formed portion is positioned at the space, at least a part of the form die is positioned at the space. Thus air in the space is kept in a state of consistently being sucked. Therefore the pulsing of the air pressure in the space can be lessened, and as a result the stack distribution of the fluid absorbent fibers can be made uniform.

In the apparatus for manufacturing an absorbent body, it is preferable that a shape of a pipe path of the duct is a shape that is wider in the direction along the moving path toward the predetermined face, the flowing path of the gas flowing through the duct toward the predetermined face is divided, by the duct-inner-wall section, into the end-side flowing path that flows through the spacing between the inner wall face and the duct-inner-wall section, and the center-side flowing path that flows through the center area, and the duct-inner-wall section is a member in which a cross-sectional shape is an abbreviated triangle shape and includes a first face facing the center area, a second face facing the gap, and a third face facing the inner wall face of the duct.

According to this apparatus for manufacturing an absorbent body, the duct-inner-wall section includes the first face, the second face, and the third face. Thus, even the shape of the pipe path of the duct is a widened shape as described above, the three faces can respectively face the center area, the gap, and the inner wall face as targets for facing without fault.

As a result, it is possible to restrict efficiently the outside air intruding through the gap flowing into the center area by the second face. Also the center-side flowing path and the end-side flowing path can be respectively formed by the first face and the second face without fault. Thus formation of a stagnation point of the gas and retention of the fluid absorbent fibers and the superabsorbent polymer inside the duct can be effectively prevented.

In the apparatus for manufacturing an absorbent body, it is preferable that the predetermined member is a rotating drum that continuously rotates in one direction of a circumferential direction, the recessed form die is formed on an outer circumferential surface of the rotating drum as the predetermined face, moved by the rotation of the rotating drum in the circumferential direction in a path along the circumferential direction as the moving path, and the opening section of the duct is provided by facing the outer circumferential surface of the rotating drum on the predetermined position in the circumferential direction.

According to this apparatus for manufacturing an absorbent body, effects of the invention of the present application can be achieved in an effective manner.

Also a method for manufacturing an absorbent body, including:

forming an absorbent body by stacking fluid absorbent fibers and a superabsorbent polymer in a gas in a form die, in the case of the form die passing a duct position, by sucking the gas through air intake holes in a bottom section of the form die using a recessed form die formed on a predetermined face of a predetermined member, moving in one direction along a moving path along the predetermined face;

a duct disposed in a predetermined position in the moving path, discharging the gas including the fluid absorbent fibers from an opening section toward the predetermined face; and a polymer casting member disposed inside the duct, casting the superabsorbent polymer from a casting opening toward a center area of the opening section in a direction along the moving path, wherein an air pressure inside the duct is made lower than the air pressure outside the duct because of the gas being sucked through the bottom section of the form die, wherein a duct-inner-wall section is inside the duct and is disposed facing an inner wall face of a wall section of the duct with a spacing therebetween, the wall section having a gap between the predetermined face and the opening section of the duct, and an outside air intrudes into the duct along the moving path through the gap, and the duct-inner-wall section restricts the outside air intruding into the duct through the gap flowing into the center area of the duct.

According to this method for manufacturing an absorbent body, in which a duct-inner-wall section is included, the duct-inner-wall section can prevent the outside air intruding into the duct through the gap flowing into the center area of the duct. Thus, effects of turbulence or the like caused by the intruding outside air can be suppressed efficiently in the center area where the superabsorbent polymer is being casted, and as a result the uniform dispersion of the superabsorbent polymer can be performed.

Embodiments

Figure 2:
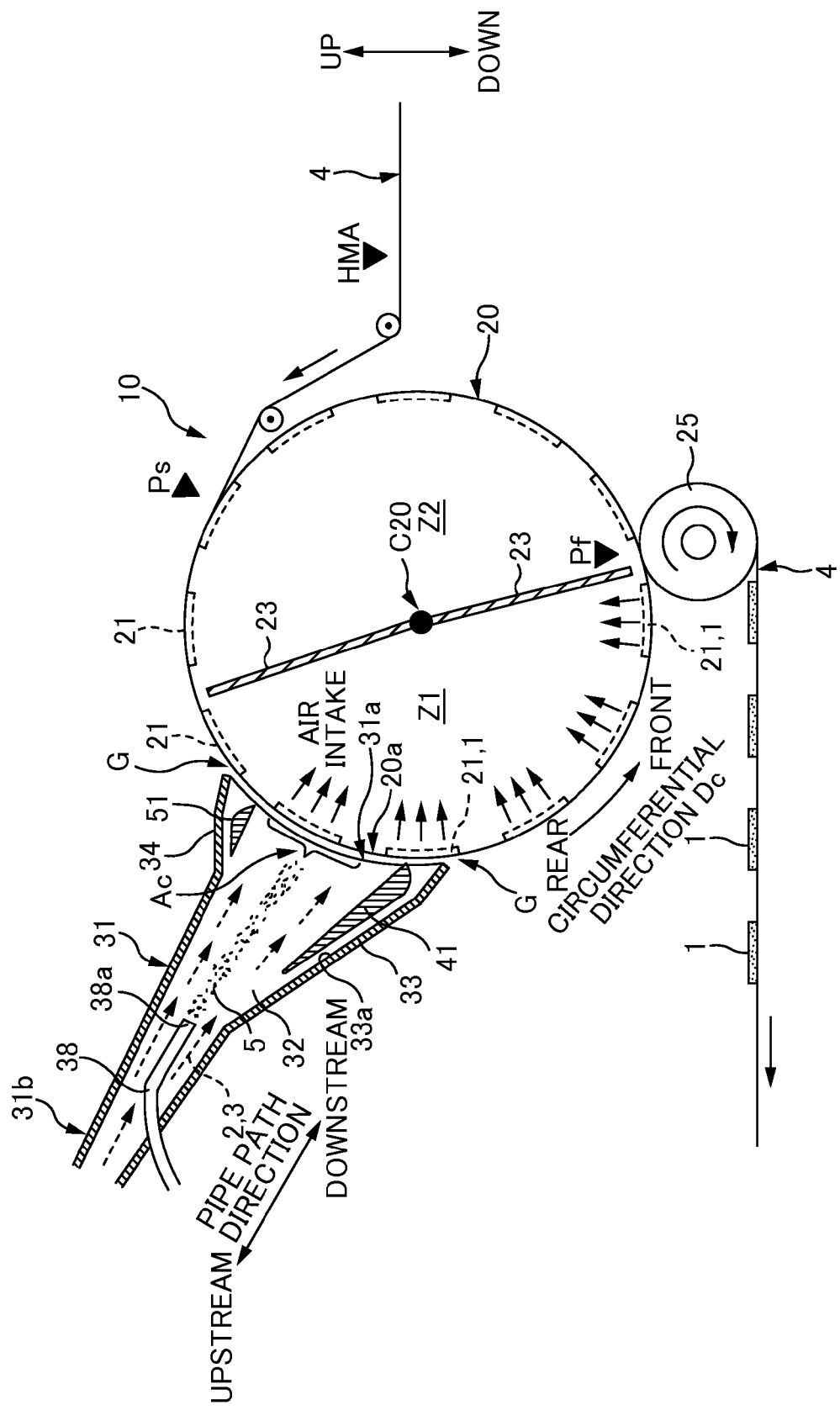
FIG. 2 is a side view of an apparatus for manufacturing 10 an absorbent body 1 according to present embodiment.

FIG. 2 is a side view of an apparatus for manufacturing 10 an absorbent body 1 according to present embodiment. And in this FIG. 2, only a part of a duct 31 of the manufacturing apparatus 10 is shown in a vertical cross-section.

The apparatus for manufacturing 10 the absorbent body 1 according to the present embodiment is a so-called fiber stacking apparatus, which stacks pulp fibers 2 as fluid absorbent fibers and thereby forms the absorbent body 1. As for main configurations, the manufacturing apparatus 10 includes (1) a rotating drum 20 (corresponds to a predetermined member) that continuously rotates in one direction of a circumferential direction Dc (for example, counterclockwise direction) about a horizontal axis C20, (2) the duct 31 that discharges an air mixture 3 (corresponds to a gas) including the pulp fibers 2 from a distribution opening 31a (corresponds to an opening section) disposed at a predetermined position in the circumferential direction Dc of the rotating drum 20 toward an outer circumferential surface 20a of the rotating drum 20, and (3) a polymer casting pipe 38 (corresponds to a polymer casting member) disposed inside the duct 31 and casts a superabsorbent polymer 5 from a casting opening 38a toward the outer circumferential surface 20a.

Note that, hereinafter, the circumferential direction Dc of the rotating drum 20 is simply referred to as a "circumferential direction" or a "front and rear direction", and a direction along the horizontal axis C20 of the rotating drum 20 (direction piercing a paper surface in FIG. 2) is referred to as a "width direction" or a "right and left direction". And a direction in which the air mixture 3 flows through the duct 31 is referred to as a pipe path direction, an upstream side in pipe path or a downstream side in pipe path.

A main body of the rotating drum 20 is a cylinder body that includes the horizontal axis C20 in a center, and recessed form dies 21 corresponding to a shape of the absorbent body 1 to be formed are intermittently formed on the outer circumferential surface 20a of the rotating drum 20 (corresponds to a predetermined face) at a predetermined pitch in the circumferential direction Dc, and many air intake holes (not shown) are formed at a bottom section of each form dies 21. On the other hand, a space inside the rotating drum 20 is divided into zones by a division wall 23 and a decompression device not shown is connected to a first zone Z1 shown in FIG. 2, thereby the first zone Z1 is maintained in a negative pressure state lower than a pressure of outside air. Thus, the form die 21 sucks an air through the air intake holes when moving through the position corresponding to the first zone Z1 on the outer circumferential surface 20a. However a second zone Z2 is not connected to the decompression device, therefore the air intake of the form die 21 will stop when the form die 21 enters the position corresponding to the second zone Z2 on the outer circumferential surface 20a. The distribution opening 31a of the duct 31 is disposed in the first zone Z1, and a release position Pf for releasing the absorbent article 1 from the form die 21 is set in the second zone Z2.

The duct 31 is a tubular member with an approximately rectangular cross section and is disposed obliquely above the rotating drum 20, and mainly includes a pair of side wall sections 32 disposed at right and left in the width direction, a front wall section 33 and a rear wall section 34 disposed at front and rear in the circumferential direction Dc. Here, a shape of the side wall section 32 becomes wider in the circumferential direction Dc from the upstream side in the pipe path toward the downstream side in the pipe path as shown in FIG. 2. Thus a cross-sectional shape of a cross section of the pipe path approximately parallel to the distribution opening 31a as an opening section in the downstream side of the duct 31 becomes larger from the upstream side in the pipe path toward the downstream side in the pipe path. That is, a shape of the pipe path of the duct 31 becomes wider in the circumferential direction Dc toward the outer circumferential surface 20a of the rotating drum 20.

The distribution opening 31a of the duct 31 covers an approximately obliquely upper portion of the outer circumferential surface 20a of the rotating drum 20 over a predetermined range. Moreover, the pulp fibers 2 that have been ground by a grinder (not shown) or the like are supplied from an upper end opening 31b of the duct 31 by riding on an air flow 3. Thus, inside the duct 31, the air mixture 3 in which the pulp fibers 2 are mixed flows from the upper, which is the upstream side in the pipe path, to the lower distribution opening 31a, which is the downstream side in the pipe path.

Thus, in the case of the form die 21, with a driving rotation of the rotating drum 20, passing the position of the distribution opening 31a the air mixture 3 discharged from the distribution opening 31a is sucked through the air intake holes of the form die 21, but at that time the pulp fibers 2 passing through the air intake holes are restricted, and thereby the pulp fibers 2 in the air mixture stack at the bottom section of the form die 21 and thus formed into the absorbent body 1. When the form die 21 finishes passing the position of the distribution opening 31a and reaches the release position Pf where the outer circumferential surface 20a of the rotating drum 20 faces downward, the absorbent body 1 is released from the form die 21 at the release position Pf, and are placed on a continuous sheet-like member 4, such as nonwoven fabric, tissue paper, or the like, and are transferred to next process.

Further, in case of an example in FIG. 2, a position Ps at which the sheet-like member 4 is supplied to the rotating drum 20 is set at a position that is upstream side than the duct 31 in the circumferential direction Dc of the rotating drum 20. Thus, the sheet-like member 4 that is wrapped around the outer circumferential surface 20a of the rotating drum 20 at this supply position Ps is moved in the circumferential direction Dc by rotation movement of the rotating drum 20 with the outer circumferential surface 20a almost without slipping. However, in the case of the form die 21 passing the position of the duct 31, the absorbent body 1 stacks in the portion of the sheet-like member 4 touching the form die 21. After that, when the form die 21 is moved to the release position Pf which is in a downstream side than the position where the duct 31 is disposed, the sheet-like member 4 is released from the outer circumferential surface 20a of the rotating drum 20 by a roller 25 disposed in the position Pf. And thereby the absorbent article 1 is released from the form die 21 and placed on the sheet-like member 4.

The polymer casting pipe 38 is a hose-shaped pipelike member with the casting opening 38a thereof positioned and disposed in a center of a cross-section of the pipe path of the duct 31. The casting opening 38a faces a center area Ac of the distribution opening 31a in the circumferential direction Dc. Thereby the superabsorbent polymer 5 casted through the polymer casting pipe 38 is densely distributed in a center portion of the absorbent body 1 that is stacked and formed in the form die 21 in the thickness direction (described later on). Further, a medium by which the superabsorbent polymer 5 is discharged through the polymer casting pipe 38 is an air flow flowing inside the polymer casting pipe 38. And a discharge direction of the air flow is made equal to a direction in which the air mixture 3 surrounding the casting opening 38a flows, and a discharge speed of the air flow is made faster than flow velocity of the air mixture 3 surrounding the casting opening 38a. Thus, in a process of flying toward the center area Ac, the superabsorbent polymer 5 is radially and circumferentially drafted by the air mixture 3 flowing in slow flow velocity, and thereby uniformly dispersed.

By the way, because of the above mentioned air intake through the bottom section of the form die 21, an air pressure inside the duct 31 is maintained in the state of negative pressure that is lower than the air pressure outside the duct 31 (for example, the state of negative pressure in which the air pressure inside the duct 31 is only 10 to 6 KPa lower than the air pressure outside the duct 31). Thus, the outside air intrudes into the duct 31 through the gap G between the outer circumferential surface 20a of the rotating drum 20 and the distribution opening 31a of the duct 31, and this intruding outside air causes turbulence such as a vortex inside the duct 31 and may inhibit the uniform dispersion of the superabsorbent polymer 5 described above. For example, in the case where a vortex flow is generated inside the duct 31, the superabsorbent polymer 5 and the pulp fibers 2 will be whirled by the vortex flow and as a result, may stack in the absorbent body 1 gathering and growing large to snowball.

At this point, for the purpose of plastering the gap G, a brush-type attachment-style seal member (not shown in FIG. 2, but shown in symbol 32a in FIG. 3) is fixed to each of the right and left side wall sections 32, 32 in the width direction included in the duct 31, and the brush sections suppress intrusion of the outside air by contacting the outer circumferential surface 20a of the rotating drum 20 so as to move slidingly.

Whereas, it is impossible to apply the attachment-style seal member to the front wall section 33 and the rear wall section 34 of the duct 31 because following disadvantages occur. That is, as shown in FIG. 2, there is a case that the sheet-like member 4 with a hot-melt adhesive HMA applied in advance is supplied to the rotating drum 20 for the purpose of adhering and fixing the absorbent body 1. However in such case, in the case of the sheet-like member 4 passing the position of the duct 31, the sheet-like member 4 is adhered to the attachment-style seal members of the front wall section 33 and the rear wall section 34 because of the hot-melt adhesive, and stable transportation of the sheet-like member 4 is impaired. Therefore, each gaps G of the front wall section 33 and the rear wall section 34 of the duct 31 have to be in an opened state and as a result, intrusion of the outside air along the circumferential direction Dc into the duct 31 cannot be prevented.

However, as mentioned above, the superabsorbent polymer 5 is mainly casted at the center area Ac of the distribution opening 31a in the circumferential direction Dc inside the duct 31. Thus, even in the case where the intruding outside air intrudes into the duct 31, if the intruding outside air stays away from the center area Ac and stays at end sections in the duct 31 in the circumferential direction Dc, that are, adjacent areas of the gaps G, it is considered that effects of the intruding outside air on the uniform dispersion of the superabsorbent polymer 5 will be small.

Therefore, in here, in exchange for accepting the intrusion of the outside air through the gaps G in the front wall section 33 and the rear wall section 34, duct-inner-wall sections 41 and 51 are provided inside the duct 31 so that the intruding outside air does not flow into the center area Ac. That is, an inner space of the duct 31 is divided, by these duct-inner-wall sections 41 and 51, into three areas that are an adjacent area Aa of the gap G related to the front wall section 33, an adjacent area Ab of the gap G related to the rear wall section 34, and the center area Ac as an area between these adjacent areas Aa and Ab (refer to FIG. 3) and thereby restricts the outside air intruding through the gaps G flowing into the center area Ac.

Further, basic structure and function of the duct-inner-wall sections 41 and 51 of the front wall section 33 (corresponds to the wall section positioned in a downstream side in the direction along the moving path) and the rear wall section 34 (corresponds to the wall section positioned in an upstream side in the direction along the moving path) are almost the same though their sizes vary. Thus, hereafter, the duct-inner-wall section 41 for the front wall section 33, that is, the duct-inner-wall section 41 disposed by facing an inner wall face 33a in the downstream side of the duct 31 in the circumferential direction Dc of the rotating drum 20 will be used as an example for explanation.

Figure 3:
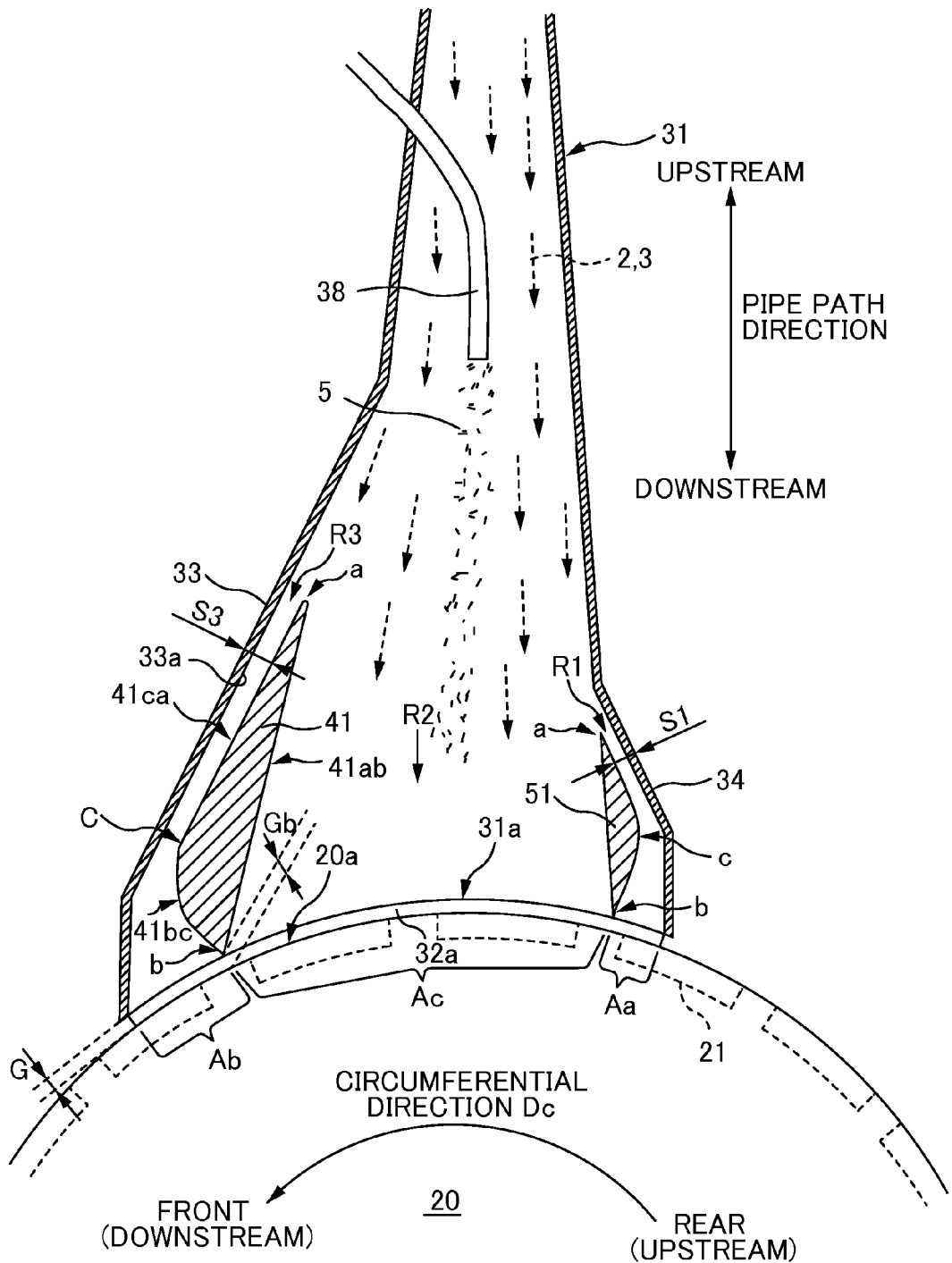
FIG. 3 is an enlarged vertical cross-sectional view of a duct-inner-wall section 41.

FIG. 3 is an enlarged vertical cross-sectional view of the duct-inner-wall section 41. For the purpose of making an easy-to-see figure, FIG. 2 is rotated about 60 degrees in a counterclockwise direction and shown as FIG. 3. In FIG. 3, the attachment-style seal member 32a of the side wall section 32 of the duct 31 is shown, but the sheet-like member 4 is not shown.

As shown in FIG. 3, the duct-inner-wall section 41 is a member with approximately same width as the front wall section 33. The vertical cross-sectional shape of the duct-inner-wall section 41 is an abbreviated triangle shape formed by connecting three triangle vertices a, b, and c with straight lines or curved lines, and the abbreviated triangle shape is maintained over the width direction. Of three sides of the abbreviated triangle shape, a face 41 ab (corresponds to a first face) related to a long side ab faces the center area Ac, a face 41bc (corresponds to a second face) related to a short side bc faces the gap G, and a face 41ca (corresponds to a third face) related to a remaining side ca (a side between the long side ab and the short side bc) faces the inner wall face 33a of the front wall section 33 of the duct 31.

And, the vertex b between the long side ab and the short side bc is disposed in the vicinity of the outer circumferential surface 20a of the rotating drum 20. For example, in here, a size of gap Gb between the vertex b and the outer circumferential surface 20a is set to 0.2 to 1 times a size of the gap G, that is, smaller than or equal to the size of the gap G. Thus, the outside air intruding through the gap G is held inside the space between the duct-inner-wall section 41 and the inner wall face 33a by the duct-inner-wall section 41 and as a result, the intruding outside air flowing into the center area Ac is restricted.

Further, the size of the forementioned gap Gb may be larger than the gap G. And in such case, if the size of the gap Gb is within a range smaller than or equal to 1.5 times the size of the gap G, though effects may become smaller than the forementioned example the inflow of the intruding outside air into the center area Ac can be suppressed. Also, it is possible to plane off corners of each vertexes a, b, and c of the duct-inner-wall section 41 by chamfering like the vertex a and the vertex c in FIG. 3, or leave the corner like the vertex b.

By the way, of the forementioned three faces 41ab, 41bc, and 41ca included in the duct-inner-wall section 41, the face 41ca facing the inner wall face 33a of the duct 31 is arranged so that the face 41ca and the inner wall face 33a are spaced apart by a spacing S3. By the duct-inner-wall section 41, a flowing path of the air mixture 3 inside the duct 31 is divided into an end-side flowing path R3 that flows through the spacing S3 between the inner wall face 33a and the duct-inner-wall section 41, and a center-side flowing path R2 that flows through the center area Ac. Also, the duct-inner-wall section 51 with same function is arranged so that the duct-inner-wall section 51 and the rear wall section 34 of the duct 31 are spaced apart by a spacing S1. Thus, the flowing path of the air mixture 3 flowing through the duct 31 toward the distribution opening 31a is divided into three paths that are, in order from the upstream side to the downstream side in the circumferential direction Dc, an end-side flowing path R1 in the rear wall section 34 side, the center-side flowing path R2, and the end-side flowing path R3 in the front wall section 33 side.

And due to such configuration, the absorbent body 1 with a three-layer structure, that is, the absorbent body 1 including an intermediate layer with a high mixture ratio of the superabsorbent polymer 5 in the middle of the absorbent body 1 in the thickness direction, and an upper layer and a lower layer with high mixture ratios of the pulp fibers 2 sandwiching the intermediate layer, can be surely manufactured.

A detailed explanation is, first, since the pulp fibers 2 are mixed in the air mixture 3, by riding on the air mixture 3 that appropriately branches at branch points of the flow paths R1, R2, and R3, in the downstream side from the branch points the pulp fibers 2 respectively flow the end-side flowing path R1 in the rear wall section 34 side, the center-side flowing path R2, and the end-side flowing path R3 in the front wall section 33 side, and reach the outer circumferential surface 20a of the rotating drum 20. That is, the pulp fibers 2 may reach the outer circumferential surface 20a through all flow paths that are the end-side flowing path R1, the center-side flowing path R2, and the end-side flowing path R3. As a result, the pulp fibers 2 are stacked in the form die 21 at entire region in the duct 31 in the circumferential direction Dc.

Whereas, the superabsorbent polymer 5 is casted toward the center area Ac as described above, and almost all of the superabsorbent polymer 5 reaches the outer circumferential surface 20a through the center-side flowing path R2 and hardly passes the end-side flowing paths R1 and R3.

Thus, in a stacking process of the absorbent body 1 into the form die 21, the form die 21 moves in the distribution opening 31a from the upstream side to the downstream side in the circumferential direction Dc. In a moving process of the form die 21, first, the pulp fibers 2 that have reached the form die 21 through the end-side flowing path R1 in the rear wall section 34 side are stacked in the form die 21. Next, the superabsorbent polymer 5 and the pulp fibers 2 that have reached the form die 21 through the center-side flowing path R2 are stacked on a pulp fiber layer in the form die 21, and thereby forming the intermediate layer with a high mixture ratio of the superabsorbent polymer 5. And finally, the pulp fibers 2 that have reached the form die 21 through the end-side flowing path R3 in the front wall section 33 side are stacked on the intermediate layer. Thus, the absorbent body 1 having a three-layered structure in the thickness direction is formed.

By the way, in foregoing description, ingenuities for the uniform dispersion of the superabsorbent polymer 5 are mainly described, however ingenuities for stacking the pulp fibers 2 while distributing uniformly are also shown in the apparatus for manufacturing 10 the absorbent body 1 according to the present embodiment. Hereafter, the four ingenuities are explained. Also in here, an explanation is made using the duct-inner-wall section 41 for the front wall section 33 of the duct 31 as an example, but same applies to the duct-inner-wall section 51 for the rear wall section 34.

Figure 4:
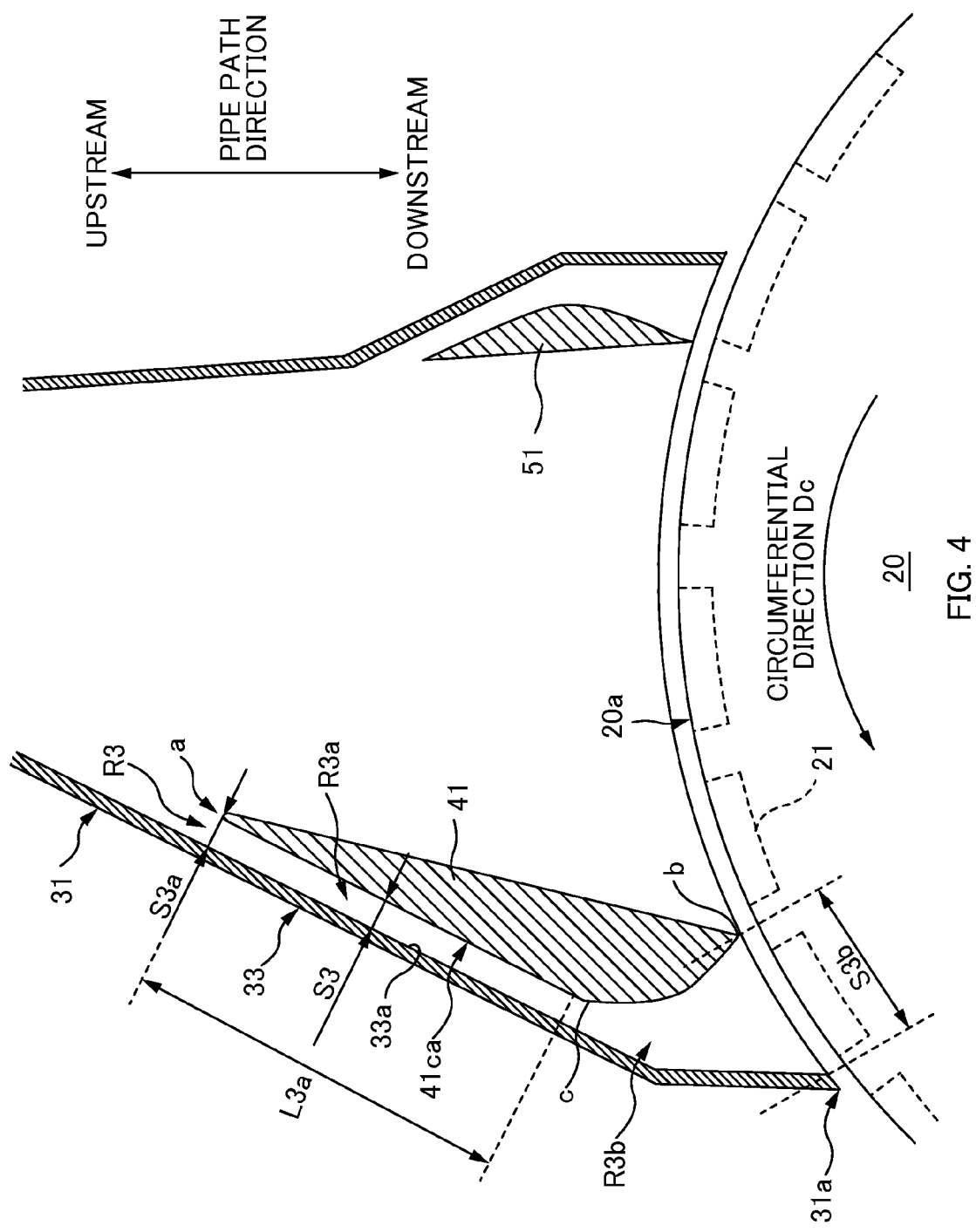
FIG. 4 is an explanatory diagram of first and second ingenuities according to uniformization of a stack distribution of pulp fibers 2.

FIG. 4 is an enlarged vertical cross-sectional view of the duct-inner-wall section 41 for the front wall section 33 of the duct 31.

First ingenuity corresponds to the spacing S3 between the inner wall face 33a of the duct 31 and the face 41ca of the duct-inner-wall section 41, in detail, a spacing S3a of an end section in a upstream side in the end-side flowing path R3 is made narrower than a spacing S3b of an end section in a downstream side.

By configuring in this way, first, in the case of the air mixture 3 passing the end section in the upstream side, because of the narrow spacing S3 (S3a) flowing speed of the air mixture 3 increases and the flow becomes stable. The spacing S3 (S3b) is wider in the end section in the downstream side, but the increased flowing speed is largely maintained because of the adjacent form die 21 sucking the air mixture 3 on the outer circumferential surface 20a of the rotating drum 20. That is, the flow of the air mixture 3 is kept in the stable state. As a result, the end section in the downstream side, that is, a space in the vicinity of the outer circumferential surface 20a of the rotating drum 20 becomes free from generation of turbulence and the stack distribution of the pulp fibers 2 can be made uniform.

Here, it is preferable to set the ratio between the spacing S3b and the spacing S3a (=S3b/S3a) within a range from 2 to 6. In this way, by making the ratio more than or equal to 2, the generation of the turbulence can be suppressed more efficiently.

Further, in an example of FIG. 4, the spacing S3a is a distance between the vertex a of the duct-inner-wall section 41 and the inner wall face 33a. The spacing S3b is a distance between the vertex b of the duct-inner-wall section 41 and the distribution opening 31a in the inner wall face 33a.

Second ingenuity also corresponds to the spacing S3. That is, in a downstream-side portion R3b in the end-side flowing path R3, the spacing S3 gradually becomes wider toward the downstream side. But an upstream-side portion R3a in the end-side flowing path R3 includes a portion having a uniform spacing S3 over a predetermined length L3a in a direction along the flowing path. In an example in FIG. 4, a portion of the inner wall face 33a located at the upstream-side portion R3a is a plane. And corresponding to this, the face 41ca of the duct-inner-wall section 41 is formed as a plane and is disposed parallel to the portion of the inner wall face 33a. Thus, the portion having the uniform spacing S3 is formed.

In this way, the flow of the air mixture 3 is fixed and stabilized while flowing through the portion having the uniform spacing S3, that is, is in a state of approximate laminar flow and reaches the form die 21 of the rotating drum 20 in the state of approximate laminar flow, and thereby the pulp fibers 2 are uniformly stacked.

Further, it is preferable to set the ratio between the predetermined length L3a and the spacing S3 (=L3a/S3) within a range from 5 to 10. In this way, by making the ratio more than or equal to 5, the laminar flow can be generated efficiently.

Figure 5:
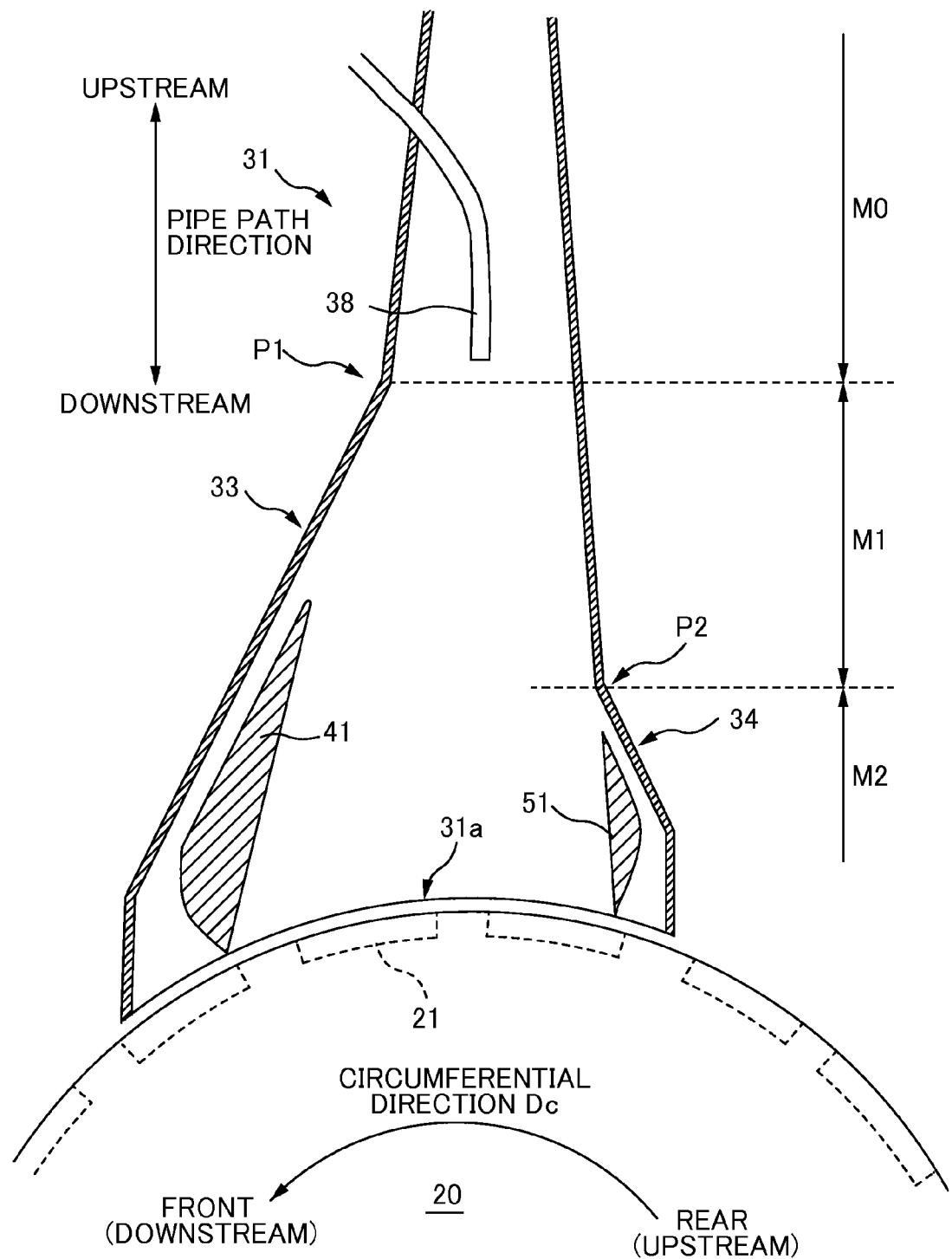
FIG. 5 is an explanatory diagram of third ingenuity according to the uniformization of the stack distribution of the pulp fibers 2.

Third ingenuity corresponds to positions where the duct-inner-wall sections 41 and 51 are located. Generally, the turbulence is apt to occur in a portion in which the cross-sectional shape of the pipe path rapidly enlarges. At this point, as shown in FIG. 5, in the shape of the pipe path of the duct 31 according to the present embodiment, area of a cross section of the pipe path is enlarged at a predetermined enlargement ratio M0 up to a predetermined first position P1 in the pipe path direction toward the distribution opening 31a. However the enlargement ratio increases from M0 to M1 from the first position P1 toward the downstream side, and the enlargement ratio increases from M1 to M2 from a second position P2 toward the further downstream side, and thus the shape becomes larger.

Here, the increase of the enlargement ratio at the first position P1 occurs because of the front wall section 33 swelling out in the downstream side in the circumferential direction Dc starting from the first position P1. Further, the increase of the enlargement ratio at the second position P2 occurs because of the rear wall section 34 swelling out in the upstream side in the circumferential direction Dc starting from the second position P2.

Thus, in a region swelling out in the circumferential direction Dc starting at the first position P1 (corresponds to a swelling-out start position), the duct-inner-wall section 41 is disposed in a position downstream side than the position P1 in the pipe path. And in this way the duct-inner-wall section 41 fills the space in the region swelling out (corresponds to a predetermined region). Also, in a region swelling out in the circumferential direction Dc starting at the second position P2 (corresponds to a swelling-out start position), the duct-inner-wall section 51 is disposed in the position downstream side than the position P2 in the pipe path. And in this way, the duct-inner-wall section 51 fills the space in the region swelling out. Thus, extreme increase of the area of a flowing-path cross section in the end-side flowing path R3 in the front wall section 33 side, the center-side flowing path R2, and the end-side flowing path R1 in the rear wall section 34 side is suppressed, and generation of the turbulence in each flowing path is restricted.

Figure 6A:
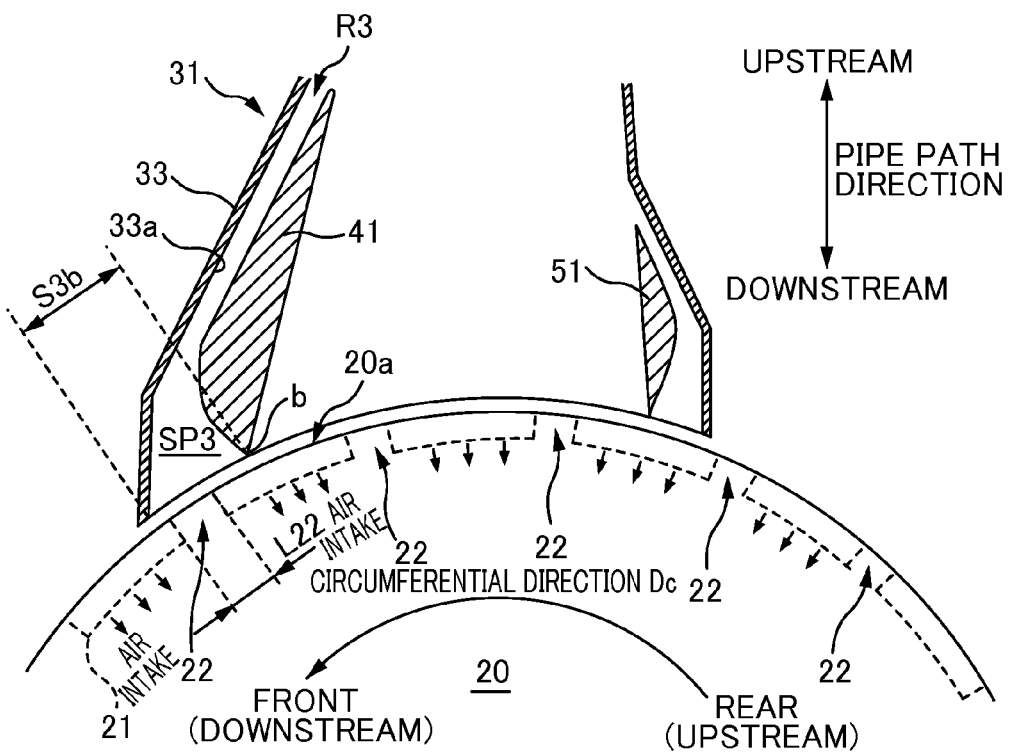
FIGS. 6A and 6B are explanatory diagrams of forth ingenuity according to the uniformization of the stack distribution of the pulp fibers 2.

Forth ingenuity corresponds to, as shown in FIG. 6A, a magnitude relation between a length L22 of a non-form-die-formed portion 22 of the form die 21 in the circumferential direction Dc, and the non-form-die-formed portion 22 is between the form dies 21, 21 on the outer circumferential surface 20a of the rotating drum 20, and a spacing S3b between the vertex b as an end portion of the duct-inner-wall section 41 in the outer circumferential surface 20a side, and an end portion of the inner wall face 33a of the duct 31 in the outer circumferential surface 20a side. And in the forth ingenuity, the former length L22 of the non-form-die-formed portion 22 is made shorter than the latter spacing S3b.

And in this way, pulsing of air pressure in the space SP3 of the spacing S3b that may be generated while the form die 21 moves in the circumferential direction Dc can be lessened. As a result, the generation of the turbulence in the space SP3 is prevented, and the stack distribution of the pulp fibers 2 can be made uniform.

Figure 6B:
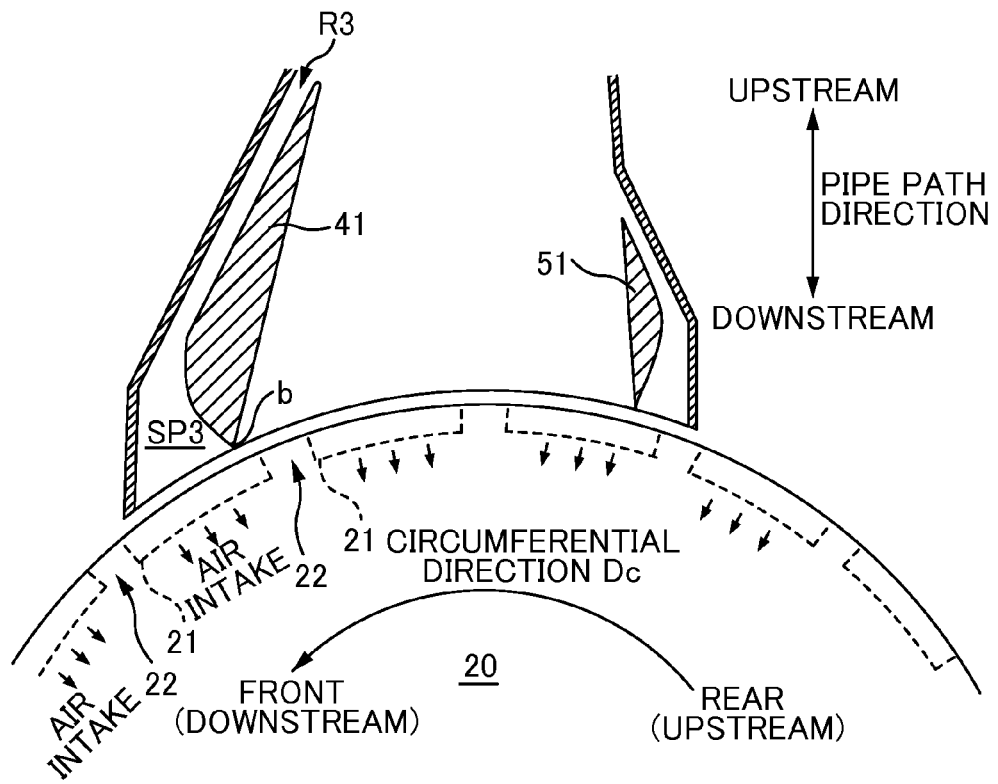
Figure 7:
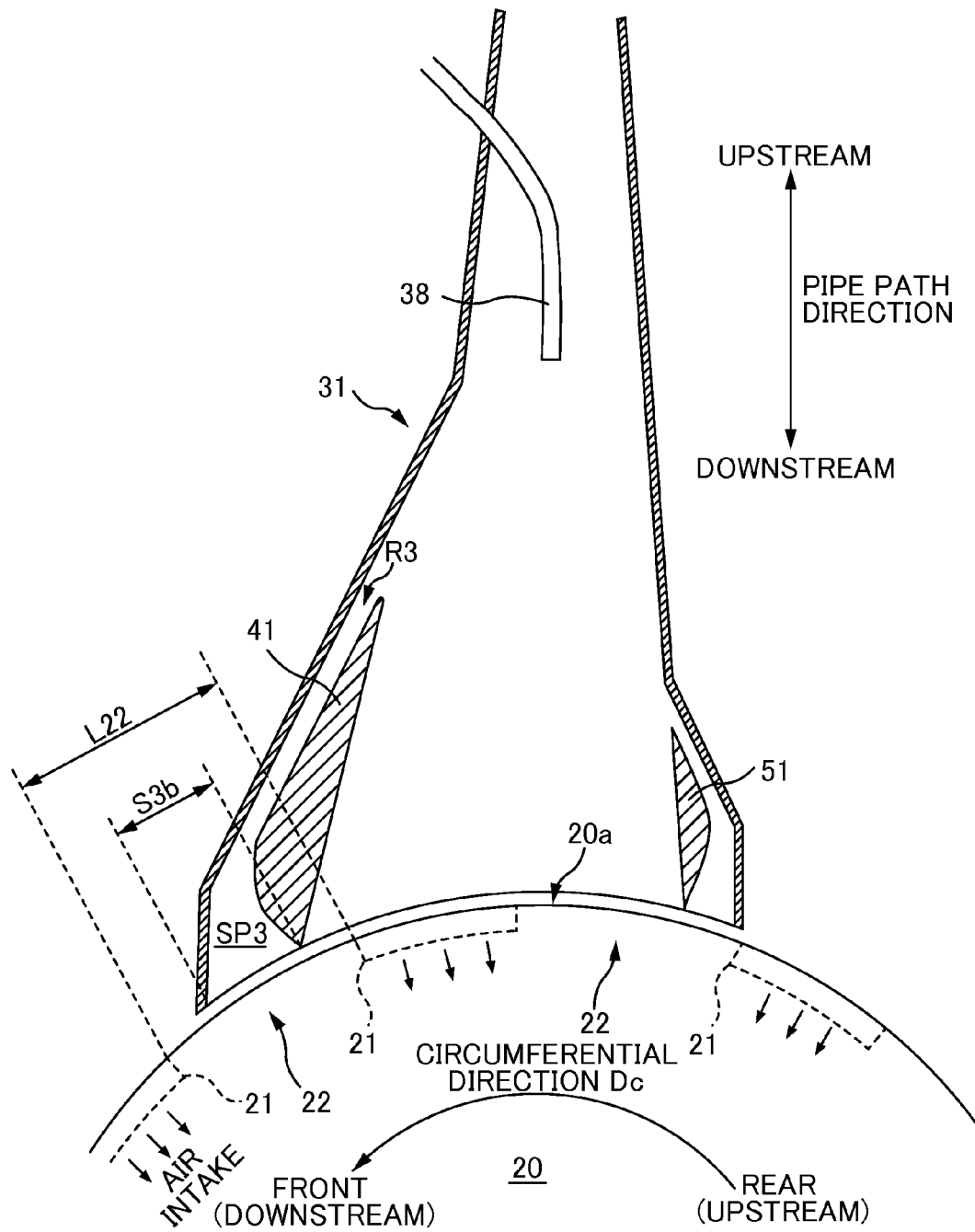
FIG. 7 is an explanatory diagram of forth ingenuity according to the uniformization of the stack distribution of the pulp fibers 2.

Detail is as follows. First, in the above rotating drum 20, the air intake is performed through the form die 21, however the air intake is not performed through the non-form-die-formed portion 22 between the form dies 21, 21 since the non-form-die-formed portion 22 is impervious to air. Thus, as shown in FIG. 6B, an atmospheric pressure in the space SP3 in the downstream side in the end-side flowing path R3 decreases in the case of the form die 21 passing, and as shown in FIG. 6A, increases in the case of the non-form-die-formed portion 22 passing. And, this periodical change in the atmospheric pressure becomes greater especially in a case where the non-form-die-formed portion 22 covers the space SP3 in the downstream side in the end-side flowing path R3, as shown in FIG. 7, thus causing a state in which none of the air is sucked from the space SP3.

In such respect, as shown in FIG. 6A, by making the length of the spacing S3b of the end section in the downstream side in the end-side flowing path R3 longer than the length L22 of the non-form-die-formed portion 22, the space SP3 in the downstream side in the end-side flowing path R3 is consistently covered by at least a part of the form die 21. That is, in the case of the non-form-die-formed portion 22 being positioned in the space SP3 in the downstream side in the end-side flowing path R3, as shown in FIG. 6A, at least a part of the form die 21 is positioned in the space SP3. Thus, the air in the space SP3 is kept in a state of consistently being sucked. Thereby the pulsing of the air pressure in the space SP3 is lessened, and as a result the stack distribution of the pulp fibers 2 can be made uniform.

Other Embodiments

In the description above, embodiments of the invention were described. However, the invention is not limited to these embodiments, and modifications as described below are possible.

In the foregoing embodiment, the wall section in which the vertical cross-sectional shape is an abbreviated triangle shape is shown as an example of the duct-inner-wall sections 41, 51. However, the shape is not limited to this. For example, a flat plate with a rectangular vertical cross-sectional shape is possible. Further, in the case of the abbreviated triangle shape, any of the long side ab, short side bc, and side ca can be either straight line or curved line, or one or two of the lines can be either the straight line or the curved line.

In the foregoing embodiment, the duct-inner-wall sections 41, 51 are respectively provided to both of the front wall section 33 and the rear wall section 34 of the duct 31. However the duct-inner-wall section can be only provided to either one. But in such case the intruding outside air affects the center area Ac more easily compared to the case in which the duct-inner-wall sections are provided to the both wall sections. Thus it is preferable to provide the duct-inner-wall sections to the both wall sections.

In the foregoing embodiment, nothing was mentioned of the size of the gap G between the distribution opening 31a of the duct 31 and the outer circumferential surface 20a of the rotating drum 20 (refer to FIG. 3), however this gap G is set as an arbitrary value within a range from 3 to 10 mm, for example.

In the foregoing embodiment, as shown in FIG. 5, the duct 31 was swelling out in the straight-line form in the circumferential direction Dc based on the predetermined enlargement ratio starting at the first position P1 and the second position P2. However, the shape of the region swelling out is not limited to this straight-line form. And a curved-line form or a polygonal-line form including a plurality of straight lines is possible.

In the foregoing embodiment, the air 3 is given as an example of a gas discharged from the duct 31. However, there is no limitation to this and the air 3 may be any sort of gas as long as it can be mixed with the fluid absorbent fiber without causing any chemical reaction with the fiber, thus nitrogen or the like is possible.

In the foregoing embodiment, the configuration is shown as an example in which the form die 21 is formed on the outer circumferential surface 20a of the rotating drum 20, and the moving path of the form die 21 is the circumferential direction Dc of the rotating drum 20. However, there is no limitation to this and any configuration is possible as long as the form die 21 moves in one direction along a predetermined moving path. For example, a conveyer belt as a predetermined member that has recessed form dies 21 formed on its belt face (corresponds to a predetermined face), and the belt being moved in a predetermined orbit and the duct 31 is disposed in a predetermined position on the orbit is possible.

In the foregoing embodiment, the pulp fibers 2 (pulp that has been ground into fibers) were described as an example of the fluid absorbent fibers. However, cellulose such as cotton, regenerated cellulose such as rayon and fibrillated rayon, semi-synthetic cellulose such as acetate and triacetate, fibrous polymers, and thermoplastic fibers may also be used, or may also be used in combination.

Reference Signs List

1 absorbent body, 2 pulp fibers (fluid absorbent fibers), 3 air mixture (gas), 4 sheet-like member, 5 superabsorbent polymer, 10 fiber stacking apparatus (apparatus for manufacturing absorbent body), 10a fiber stacking apparatus, 20 rotating drum (predetermined member), 20a outer circumferential surface (predetermined face), 21 form die, 22 non-form-die-formed portion, 23 division wall, 25 roller, 31 duct, 31a distribution opening (opening section), 31b upper end opening, 32 side wall section, 32a attachment-style seal member, 33 front wall section (duct wall section, wall section positioned in downstream side in moving path), 33a inner wall face, 34 rear wall section (duct wall section, wall section positioned in upstream side in moving path), 38 polymer casting pipe (polymer casting member), 38a casting opening, 41 duct-inner-wall section, 41ab face (first face), 41bc face (second face), 41ca face (third face), 51 duct-inner-wall section, G gap, a vertex, b vertex, c vertex, Aa adjacent area, Ab adjacent area, Ac center area, Gb gap, P1 first position (swelling-out start position), P2 second position (swelling-out start position), Pf release position, Ps supply position, R1 end-side flowing path, R2 center-side flowing path, R3 end-side flowing path, R3a upstream-side portion in end-side flowing path, R3b downstream-side portion in end-side flowing path, S1 spacing, S3 spacing, S3a spacing, S3b spacing, Z1 first zone, Z2 second zone, C20 horizontal axis, SP3 space

The invention claimed is:

1. An apparatus for manufacturing an absorbent body, comprising:

a recessed form die formed on a predetermined face of a predetermined member, moving in one direction along a moving path along the predetermined face;

a duct disposed in a predetermined position in the moving path, discharging a gas including fluid absorbent fibers from an opening section toward the predetermined face; and a polymer casting member disposed inside the duct, casting a superabsorbent polymer from a casting opening toward a center area of the opening section in a direction along the moving path, wherein in the case of the form die passing the duct position, by the gas being sucked through air intake holes in a bottom section of the form die, the fluid absorbent fibers and the superabsorbent polymer in the gas are stacked in the form die to form an absorbent body, wherein an air pressure inside the duct is made lower than the air pressure outside the duct because of the gas being sucked through the bottom section of the form die, wherein a first duct-inner-wall section is inside the duct and is disposed facing an inner wall face of a wall section of the duct with a spacing therebetween, the wall section having a first gap between the predetermined face and the opening section of the duct, the first duct-inner-wall section facing the inner wall face of the wall section positioned in an upstream side in the direction along the moving path, a second duct-inner-wall section provided inside the duct and disposed so as to face the inner wall face of the wall section of the duct with a spacing therebetween, the wall section having a second gap between the predetermined face and the opening section of the duct, the second duct-inner-wall having a different size than a size of the first duct-inner-wall, the second duct-inner-wall section facing the inner wall face of the wall section positioned in a downstream side in the direction along the moving path, and an outside air intrudes into the duct along the moving path through the first and second gaps, and the first duct-inner-wall section and the second duct-inner-wall section restrict the outside air intruding into the duct through the first gap and the second gap flowing toward the center area of the duct, wherein the second duct-inner-wall section is a member having a cross-sectional shape in the form of an abbreviated triangle and the abbreviated triangle includes a first face facing the central area of the duct, a second face facing the second gap, and a third face facing the inner wall face of the duct, and the second face is curved.

2. An apparatus for manufacturing an absorbent body according to claim 1, wherein a flowing path of the gas flowing through the duct toward the predetermined face is divided, by the first and second duct-inner-wall sections, into an end-side flowing path that flows through the spacing between the inner wall face and the first and second duct-inner-wall sections, and a center-side flowing path that flows through the center area of the duct, and in the end-side flowing path, the spacing of an end section in an upstream side is made narrower than the spacing of an end section in a downstream side.

3. An apparatus for manufacturing an absorbent body according to claim 1 wherein a flowing path of the gas flowing through the duct toward the predetermined face is divided, by the first and second duct-inner-wall sections, into an end-side flowing path that flows through the spacing between the inner wall face and the first and second duct-inner-wall sections, and a center-side flowing path that flows through the center area, and in a portion in a downstream side in the end-side flowing path the spacing becomes wider toward the downstream side, and in a portion in an upstream side in the end-side flowing path a portion having an uniform spacing over a predetermined length along the flowing path is included.

4. An apparatus for manufacturing an absorbent body according to claim 1, wherein the first and second duct-inner-wall sections are respectively provided to the wall section positioned in an upstream side in the direction along the moving path and the wall section positioned in a downstream side, of the wall sections of the duct, and a flowing path of the gas flowing through the duct toward the predetermined face is divided into three, by the first and second duct-inner-wall sections, in respect to the direction along the moving path.

5. An apparatus for manufacturing an absorbent body according to claim 1, wherein the wall section of the duct is formed in a shape in which a predetermined region of the wall section is swelling out in the direction along the moving path than a surrounding region, a predetermined swelling out region is positioned in the predetermined face side starting at a predetermined swelling-out start position, the first and second duct-inner-wall sections are provided in the position in the predetermined face side than the swelling-out start position, and a space in the predetermined swelling out region is filled by the first and second duct-inner-wall sections, and at a same time a flowing path of the gas flowing through the duct toward the predetermined face is divided, by the first and second duct-inner-wall sections, into an end-side flowing path that flows through a spacing between the inner wall face and the first and second duct-inner-wall sections, and a center-side flowing path that flows through the center area.

6. An apparatus for manufacturing an absorbent body according to claim 1, wherein a plurality of the form dies are intermittently formed in the direction along the moving path, a portion in which the form die is not formed between the form dies on the predetermined face is impervious to air, and size of a spacing between an end portion of the first and second duct-inner-wall sections in the predetermined face side and an end portion of the inner wall face of the duct in the predetermined face side is longer than a length of the above mentioned non-form-die-formed portion in the direction along the moving path.

7. An apparatus for manufacturing an absorbent body according to claim 1, wherein a shape of a pipe path of the duct is a shape that is wider in the direction along the moving path toward the predetermined face, the flowing path of the gas flowing through the duct toward the predetermined face is divided, by the first duct-inner-wall section, into the end-side flowing path that flows through the spacing between the inner wall face and the first duct-inner-wall section, and the center-side flowing path that flows through the center area of the duct, and the first duct-inner-wall section is a member in which a cross-sectional shape is an abbreviated triangle shape and the abbreviated triangle includes a first face facing the center area, a second face facing the first gap, and a third face facing the inner wall face of the duct.

8. An apparatus for manufacturing an absorbent body according to claim 1, wherein the predetermined member is a rotating drum that continuously rotates in one direction of a circumferential direction, the recessed form die is formed on an outer circumferential surface of the rotating drum as the predetermined face, moved by the rotation of the rotating drum in the circumferential direction in a path along the circumferential direction as the moving path, and the opening section of the duct is provided by facing the outer circumferential surface of the rotating drum on the predetermined position in the circumferential direction.

* * * * *